US010369213B2

(12) United States Patent
Bhambhani et al.

(10) Patent No.: US 10,369,213 B2
(45) Date of Patent: *Aug. 6, 2019

(54) THERMOSTABLE RESPIRATORY SYNCTIAL VIRUS (RSV) VACCINE COMPOSITIONS

(71) Applicant: Merck Sharp & Dohme Corp., Rahway, NJ (US)

(72) Inventors: Akhilesh Bhambhani, Doylestown, PA (US); Robert K. Evans, Bangor, ME (US); Lynne A. Isopi, Sellersville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 77 days.

This patent is subject to a terminal disclaimer.

(21) Appl. No.: 15/029,064

(22) PCT Filed: Oct. 13, 2014

(86) PCT No.: PCT/US2014/060233
§ 371 (c)(1),
(2) Date: Apr. 13, 2016

(87) PCT Pub. No.: WO2015/057548
PCT Pub. Date: Apr. 23, 2015

(65) Prior Publication Data
US 2016/0250319 A1    Sep. 1, 2016

Related U.S. Application Data

(60) Provisional application No. 61/891,530, filed on Oct. 16, 2013.

(51) Int. Cl.
*A61K 39/155* (2006.01)
*A61K 39/12* (2006.01)
*A61K 9/19* (2006.01)
*A61K 47/26* (2006.01)
*C12N 7/00* (2006.01)
*A61K 39/00* (2006.01)

(52) U.S. Cl.
CPC .............. *A61K 39/155* (2013.01); *A61K 9/19* (2013.01); *A61K 39/12* (2013.01); *A61K 47/26* (2013.01); *C12N 7/00* (2013.01); *A61K 2039/5254* (2013.01); *C12N 2760/18521* (2013.01); *C12N 2760/18534* (2013.01); *C12N 2760/18551* (2013.01)

(58) Field of Classification Search
None
See application file for complete search history.

(56) References Cited

U.S. PATENT DOCUMENTS

| 4,389,794 A | 6/1983 | Bitterly |
| 4,664,924 A | 5/1987 | Sugisawn et al. |
| 4,809,596 A | 3/1989 | Akutsu et al. |
| 4,882,851 A | 11/1989 | Wennerstrum et al. |
| 5,565,318 A | 10/1996 | Walker et al. |
| 6,128,321 A | 10/2000 | Bennett et al. |
| 6,956,865 B1 | 10/2005 | Khaunte et al. |
| 9,782,470 B2 * | 10/2017 | Bhambhani ............ A61K 47/26 |
| 2010/0218395 A1 | 9/2010 | Durante et al. |
| 2010/0260796 A1 | 10/2010 | Belin-Poput et al. |
| 2010/0297231 A1 | 11/2010 | Vehring |
| 2011/0064723 A1 | 3/2011 | Truong-Le et al. |
| 2011/0212130 A1 | 9/2011 | Yagodich et al. |
| 2011/0243988 A1 | 10/2011 | Ohtake et al. |
| 2012/0291305 A1 | 11/2012 | Fu et al. |
| 2013/0189304 A1 * | 7/2013 | Truong-Le ........... A61K 9/0019 424/209.1 |
| 2014/0017318 A1 | 1/2014 | O'Connell et al. |

FOREIGN PATENT DOCUMENTS

| WO | WO2002103407 A2 | 12/2002 |
| WO | WO2008092228 | 8/2008 |
| WO | WO2009033285 A1 | 3/2009 |
| WO | WO2009049409 A1 | 4/2009 |
| WO | WO 2013/010257 * | 1/2013 |
| WO | WO2013010257 A1 | 1/2013 |
| WO | WO2013066769 A1 | 5/2013 |
| WO | WO2014009328 A1 | 1/2014 |
| WO | WO2015057540 A1 | 4/2015 |
| WO | WO2015057541 A1 | 4/2015 |

OTHER PUBLICATIONS

James Patrick Dolan Jr., Use of Volumetric Heating to Improve Heat Transfer During Vial Freeze-Drying, Dissertation submitted to the Faculty of the Virginia Polytechnic Institute and State University in partial fulfillment of the requirements for the degree of Doctor of Philosophy in Mechanical Engineering, 1998, URL:https://theses.lib.vt.edu/theses/available/etd-82298-162911unrestricted/etd_2008.pdf.

Bhambhani, Akhilesh; "Lyophilization Strategies for Development of a High-Concentration Monoclonal Antibody Formulation: Benefits and Pitfalls"; Am. Pharm. Review; 2010; 31-38; 13(1).

Gupta, Chander Kanta, et al.; "Stabilization of respiratory syncytial virus (RSV) against thermal inactivation and freeze-thaw cycles for development and control of RSV vaccines and immune globulin"; Vaccine; 1996; 1417-1420; 14.

(Continued)

*Primary Examiner* — Shanon A. Foley
*Assistant Examiner* — Myron G Hill
(74) *Attorney, Agent, or Firm* — Andrew W. Custer; Laura M. Ginkel

(57) ABSTRACT

Methods for improving the drying yield and stability of RSV vaccines comprising a highly thermolabile enveloped live virus and/or one or more RSV protein subunits, are described. Methods for rapid drying of RSV formulations containing between 17.5% and 60% w/w of a non-polymeric sugar and using either conduction or radiation dominant drying mechanisms, are disclosed. The disclosed methods provide for; 1) a dried RSV formulation with improved stability profile; 2) faster drying; and 3) integration of dried RSV into a primary device (such as dual chamber cartridges, foil-pouch devices etc.), pre- as well as post-drying.

9 Claims, No Drawings

(56) References Cited

OTHER PUBLICATIONS

Law, T.J., et al.; "The Stabilizing Effect of Sucrose upon Respiratory Syncytial Virus Infectivity (33054)"; Experimental Biology and Medicine; 1968; 515-518; 128.

McAdams, David, et al.; "Spray drying and vaccine stabilization"; Expert Rev. Vaccines; 2012; 1211-1219; 11(10).

Rigter, Alan, et al.; "A Protective and Safe Intranasal RSV Vaccine Based on a Recombinant Prefusion-Like Form of the F Protein Bound to Bacterium-Like Particles"; PLos One; 2013; e71072 (1-14); 8(8).

Seo, Jeong-Ah, et al.; "Making monosaccharide and disaccharide sugar glasses by using microwave oven"; Journal of Non-Crystalline Solids; 2004; 111-114; 333.

Tannock, Gregory A., et al.; "Freeze-Drying of Respiratory Syncytial Viruses for Transportation and Storage"; J. Clin. Microbiol.; 1987; 1769-1771; 25(9).

Tlaxca, Jose L. et al., Live attenuated and inactivated viral vaccine formulation and nasal delivery: Potential and challenges, Advanced Drug Delivery Reviews, 2014, 56-78, 93.

Chiang et al., A microwave applicator for uniform irradiation by circularly polarized waves in an anechoic chamber, Review of Scientific Instruments, 2014, 1-5, 85.

Jones, Kathryn L. et al., Long-term storage of DNA-free RNA for use in vaccine studies, Biotechniques, 2007, 675-681, 43(5).

\* cited by examiner

ABASE RESPIRATORY
THERMOSTABLE RESPIRATORY SYNCTIAL VIRUS (RSV) VACCINE COMPOSITIONS

FIELD OF THE INVENTION

The present invention relates to live, attenuated respiratory syncytial virus (RSV) compositions and RSV protein subunit compositions that are thermostable. In particular, the present invention relates to compositions of dried RSV or RSV protein subunits which are obtained through the application of conduction-based or radiation-based drying methods and/or the combination thereof to a frozen RSV composition having a high saccharide protective matrix.

BACKGROUND OF THE INVENTION

Vaccines, including respiratory syncytial virus (RSV) vaccines, are thermolabile and to overcome the instability barrier, are typically stored in a dried state. The labile nature of vaccines renders drying of vaccines a challenging task and often requires long conservative freeze-drying cycles (typically cycle times in excess 48-72 hours) to obtain dried thermostable vaccines. The thermolabile nature of the RSV (poor drying yield and stability) renders the virus susceptible to inactivation by minimal changes in the environment associated with drying and/or incubation at elevated temperatures. Historical approaches to obtain dried vaccine and biologics hinges mostly on the use of lyophilization and to a limited extent on spray-drying. However, vaccines, even if dried using these methods, have thus far failed to achieve adequate accelerated 37° C. and long-term room temperature stability.

Lyophilization processes typically entail freezing the vaccine components and then drying by sublimation. Methods of lyophilizing biological materials have been described. In these methods, liquid is formulated and filled into a primary container (mostly glass vials), freezing using a blast freezer and lyophilizing using the conventional freeze-drying approach. Techniques for obtaining frozen, discrete beads of material (vaccine, biologics, small molecules etc.) wherein individual samples of the biological material are frozen in bead form and dried prior to placing a desired number of the dried beads into a storage container such as a glass vial have been described. See International Patent Application Publication No. WO2013/066769. Historically, these methods relied on either (a) dispensing an aliquot of a liquid composition containing the desired amount of a biological material into a container of a cryogen such as liquid nitrogen, which results in direct contact of the biological material with the cryogen and/or (b) dispensing an aliquot of a liquid composition containing the biological material into a cavity present on a chilled solid plate, where the cavity contains the aliquot until it is frozen. RSV strains are particularly difficult to freeze-dry. See, e.g., Tannock et al., 1987, J. Clin. Microbiol. 25:1769-1771.

RSV vaccines are often stored at sub-zero temperatures in the presence of high concentrations of stabilizing sugars. See, e.g., Gupta et al., 1996, Vaccine 14:1417-20. Findings suggest that RSV stability was maintained best at sucrose concentrations >30% at sub-zero temperatures with greatest stability observed at −70° C. See Law et. al., 1968, Experimental biology and Medicine 128: 515-518. Similarly, other findings revealed that stabilization of RSV at sub-zero temperature conditions in the presence of sugars (25% sucrose or 10% trehalose or 10% sorbitol) effectively maintains stability. See e.g., Gupta et al., 1996, Vaccine 14:1417-20.

U.S. Pat. No. 5,565,318 describes the use of a polymeric sugar as a protective agent in the formation of room temperature stable semi-spheres containing biologically active materials. U.S. Patent Application Publication No. 20100297231 describes foam-forming formulations comprising a biologically active protein and a polyol. U.S. Patent Application Publication No. 20110243988 describes the use of polyols as a stabilizer for dry powder live virus vaccines.

Microwave vacuum-drying (MVD) is a rapid method that can yield products, such as foods, plants and biological materials, with improved stability compared to air-dried and freeze-dried products. Because the drying is done under reduced pressure, the boiling point of water and the oxygen content of the atmosphere is lowered, so food or medicinal components sensitive to oxidation and thermal degradation can be retained to a higher degree than by air-drying. See, e.g., U.S. Pat. Nos. 4,389,794; 4,664,924; 4,809,596; 4,882,851; 6,128,321; 6,956,865; and International Patent Application Publication Nos. WO 02/103407; WO 2009/033285; WO 2009/049409; and WO2013/010257.

Seo et al., 2004, Journal of Non-Crystalline Solids, 333: 111-114 discloses a method for making sugar glass without caramelization of the sugar through the use of microwaves. International Patent Application No. PCT/EP2013/064422 describes methods of producing medicinal products by freeze-drying compositions comprising 20%-60% w/w of a non-polymeric sugar.

There is a desire for increased heat stability, especially for the developing world where transport, storage, and administration costs (mainly due to the need of continuous refrigeration, also referred to as the "cold chain") represent a significant portion of the product cost.

SUMMARY OF THE INVENTION

The present invention relates to methods for preparing respiratory syncytial virus (RSV) vaccine compositions that are thermostable (e.g., the potency $\log_{10}$ loss at 37° C. for one week storage is less than 1 as determined by a RSV plaque assay). In particular, the present invention pertains to methods for preparing dried RSV formulation through the application of lyophilization or microwave radiation in a traveling wave format to a frozen body to form a dried pellet or dried cake of RSV. The frozen body comprises a protective matrix comprising at least 17.5% saccharides in a pH range of 6 to 8. The invention also pertains to the resulting product, which in particular is a dried body comprising RSV, stabilized by sugar. The present invention also pertains to the process of integrating the pellets dried in this manner with a device or a package.

Accordingly, the present invention provides a method for drying a vaccine composition comprising a live attenuated RSV, one or more RSV protein subunits or a combination thereof, comprising the steps of: a) providing an aqueous composition in a primary container comprising live attenuated RSV, one or more RSV protein subunits or a combination thereof, a buffer, and between 17.5% w/w and 60% w/w of a non-polymeric sugar, wherein the pH of the buffer is between 6.0 and 8.0, 6.0 and 7.2, 6.0 and 7.0, or 6.0 and 6.8; b) freezing the aqueous composition, thereby forming at least one frozen body comprising the buffer in frozen form; and c) lyophilizing or microwave vacuum drying the aqueous composition. In certain embodiments, the sugar is selected from monomeric and/or dimeric sugar molecules, including glucose, galactose, maltose, sucrose, trehalose, fructose, lactose, saccharose, mannitol, sorbitol, xylitol or a combination thereof. In certain embodiments, the sugar is sucrose, trehalose or a combination thereof. The amount of the sugar in the aqueous composition can be from 20-55% w/w, 20-50% w/w, 20-45% w/w, 25-45% w/w, 25-47.5% w/w, 25-40% w/w, 30-47.5% w/w, 30-40% w/w, 25-35% w/w or 27-30% w/w. The buffer is selected from Tris, histidine, phosphate and combinations thereof.

In certain embodiments, the frozen body is a pellet or cake. A frozen pellet may be obtained by aliquoting the aqueous composition on a chilled mold or surface having a temperature less than −100° C. A frozen cake may be obtained by filling a container with the aqueous composition and subjecting the container to freezing below the glass transition temperature at a freezing rate of 0.1 to 20° C./minute.

In embodiments where MVD is used, the MVD can comprise applying microwave radiation to the frozen pellet under a pressure below atmospheric pressure in order to sublimate the composition and obtain a dried formulation. The reduced pressure can be a pressure in the range of 20 to 500 mTorr or 20 to 200 mTorr.

The present invention also provides a composition comprising: a) a live attenuated RSV, one or more RSV protein subunits, or a combination thereof; and b) between 17.5% w/w and 60% w/w of one or more non-polymeric sugars, and c) a buffer, wherein the pH of the buffer is between 6 and 8. The composition may be in the form of a dried product, for example, a dried pellet or dried cake. In one embodiment, the dried product formed is substantially similar in appearance to freeze-dried product characterized in that the dried product comprises of the vaccine dispersed in a solid matrix of the non-polymeric sugar.

The present invention also provides a device comprising a composition of the present invention, which may be in the form of a plastic vial.

Other embodiments, aspects and features of the present invention are either further described in or will be apparent from the ensuing description, examples, and appended claims.

DETAILED DESCRIPTION OF THE INVENTION

The present invention provides methods for improving the drying yield and stability of RSV vaccines comprising a highly thermolabile enveloped live virus and/or one or more RSV protein subunits. Advantages of the present invention include 1) a dried RSV formulation with improved stability profile; 2) faster drying; and 3) integration of dried RSV into a primary device (such as dual chamber cartridges, foil-pouch devices etc.), pre- as well as post-drying. In an embodiment, development of a dried RSV vaccine formulation that is stable at 37° C. for 1 week ($\log_{10}$ loss<1) with a low drying loss (<0.3 $\log_{10}$ loss) is surprising.

The present invention is based, in part, on the surprising RSV drying yield and stability obtained given the fact that the drying process induces stresses and the challenges associated with drying formulation containing high concentration of disaccharides. The preservation of biologically active protein by freeze-drying in a protective matrix comprising a sugar has been described. See U.S. Provisional Patent Application Ser. No. 61/669,797, filed on Jul. 10, 2012. However, the Examples disclosed herein suggest that optimal dried thermostable RSV formulations require the right combination of excipients at high concentration in a suitable pH range. As shown in the Examples, attainment of dried thermostable RSV formulation can be obtained using two different combinations of image/drying approaches (lyospheres/lyophilization and vial/MVD). Thermostable RSV formulations can also be obtained by lyophilization alone and other freezing methods, although drying time will be significantly longer.

Using the methods of the invention, MVD of high disaccharide formulations can be achieved in less than 12 hours (preferably less than 8 hours), while frozen high disaccharide formulation beads can be dried in less than 24 hours (preferably less than 18 hours). These methods provide a significant advantage over conventional freeze-drying of high disaccharide formulation containing vial (drying time~7 days).

The methods of the invention also provide means for integrating dried RSV formulations with storage/delivery devices. Dried RSV lyospheres can be easily integrated with novel devices while MVD allows drying of RSV formulation in novel devices through radiation dominant drying.

As used herein, the term "body" refers to an object having a volume such that it can be handled individually by hand (manually).

As used herein, the term "sublimation" refers to a process wherein materials change from a solid phase directly to a gaseous phase without passing through a liquid phase. With water, ice turns directly to water vapor without first melting to a liquid form, and then evaporating. Sublimation can occur at various temperatures and pressure combinations, but typically sublimation needs low temperatures and a vacuum pressure less than atmospheric. Sublimation provides advantages for materials processing as purity is maintained and the processed material does not have to be subjected to high temperatures, such as would be needed to boil off the water.

As used herein, the term "sugar" refers to any of a group of water-soluble carbohydrates of relatively low molecular weight and typically having a sweet taste. The term sugar includes reducing sugars (such as fructose and maltose), non-reducing sugars (such as sucrose and trehalose), sugar alcohols (such as xylitol and sorbitol) and sugar acids (such as gluconic acid and tartaric acid). A "non-polymeric sugar" refers to mono-, di-, tri-, and oligomeric sugar molecules comprising at most six monomeric sugar molecules.

All ranges set forth herein are intended to be inclusive of the lower and upper limit of the range. All values set forth herein can vary by ±1%, ±2%, ±5%, ±10%, ±15%, or ±20%, the term "about" is also meant to encompass these variations.

The aqueous composition comprises RSV, a buffer and from 17.5% w/w and 60% w/w of one or more non-polymeric sugars, wherein the pH of the buffer is between 6 and 8. RSV, as contemplated herein, can include live virus (including attenuated live RSV as described, for example, in U.S. Patent Application Publication No. 20110212130) or RSV protein subunits (for example, recombinant Fusion (F) protein as described in Rigter et al., 2013, PLos One 8:e71072. The RSV is preferably a live, attenuated RSV.

The buffer can be any carrier fluid suitable for dissolving and/or dispersing the substance to be carried. The buffer is usually selected from a pharmaceutically accepted buffer system. The preferred buffer is a pharmaceutically accepted buffer system with the ability to resist a change in pH upon addition of acid, base, inorganic compound, organic compound or other solvent or diluent. Buffering components, such as phosphate and citrate, are included to control the pH of the enveloped virus vaccine-containing solution, as well as to adjust the solution osmolarity. The buffer concentration may range from about 5 mM to about 2 M, with the pH of the solution adjusted to a range from about 6.0 to about 8.0, about 6.0 to about 7.2, about 6.0 to about 7.0, or about 6.0 to about 6.8.

A pharmaceutically acceptable buffer may be selected from the group consisting of potassium phosphate, sodium phosphate, sodium acetate, histidine, Hepes, Tris, Bis-Tris, imidazole, sodium citrate, sodium succinate, ammonium bicarbonate, and a carbonate. The buffer may comprise a pH ranging from about pH 6.0 to about pH 8.0, and also, a pH of about pH 6.0 to about pH 7.0.

The sugar is generally selected from monomeric and/or dimeric molecules, and in particular can be chosen from the group consisting of glucose, galactose, maltose, sucrose, trehalose, fructose, lactose, saccharose, mannitol, sorbitol, xylitol, dextran and combinations thereof. The amount of the sugar in the aqueous composition may range from 20-55% w/w, 20-50% w/w, 20-45% w/w, 25-45% w/w, 25-47.5% w/w, 25-40% w/w, 30-47.5% w/w, 30-40% w/w, 25-35% w/w or 27-30% w/w. Preferably, the amount of sugar is higher than 25% w/w, typically around 27-40% w/w. In specific embodiments, the sugar concentration is 17.5%, 20%, 25% or 30%. In specific embodiments, the sugar is sucrose, trehalose or a combination thereof.

The aqueous composition can further comprise surfactants, polymers, amino acids, and other pharmaceutically acceptable excipients. Polymer can be included to act as a stabilizer for the virus. Polymer concentration may range from about 0.1% to about 20% (w/v). Surfactants can be included to decrease the surface tension of the atomized droplets and to displace the virus molecules from the surface of the atomized droplets. Surfactants may also increase the solubility of other formulation components. Surfactant concentration may comprise about 0.005 to about 2% by weight of said virus vaccine-containing formulation. Plasticizers may be included to increase the interaction of the glassy matrix with the virus vaccine upon dehydration, thereby enhancing storage stability. See e.g., U.S. Pat. No. 7,101, 693. The concentration of plasticizer in the present invention may comprise about 0.2% to about 5% by weight of the formulation. Divalent cations and amino acids can be included to stabilize the virus and to adjust the pH and the osmolarity of the solution. The divalent cation concentration may range from about 0.1 mM to about 100 mM and the amino acid concentration may range from about 0.1% to about 10% (w/v).

In one embodiment, the aqueous composition comprises live RSV virus, a sugar, polymer, surfactant, amino acid and a buffer.

In another embodiment, the aqueous composition comprises one or more RSV protein subunits, a sugar, polymer, surfactant, amino acid and a buffer.

In yet another embodiment, the aqueous composition comprises live RSV virus and one or more RSV protein subunits, a sugar, polymer, surfactant, amino acid and a buffer.

A polymer can be selected from the group consisting of gelatin, hydrolyzed gelatin, collagen, chondroitin sulfate, a sialated polysaccharide, water soluble polymers, polyvinyl pyrrolidone, actin, myosin, microtubules, dynein, kinetin, bovine serum albumin, human serum albumin, lactalbumin hydrolysate, and combinations thereof. A polymer is present at a concentration ranging from about 0.1% to about 20% (w/v). In one embodiment, the polymer is gelatin present at a concentration ranging from about 0.5% to about 5% (w/v).

A surfactant can be selected from the group consisting of polyethylene glycol, polypropylene glycol, polyethylene glycol/polypropylene glycol block copolymers, polyethylene glycol alkyl ethers, polyethylene glycol sorbitan monolaurate, polypropylene glycol alkyl ethers, polyethylene glycol/polypropylene glycol ether block copolymers, polyoxyethylenesorbitan monooleate, alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde and phenol, lignin-sulfite waste liquor, alkyl phosphates, quaternary ammonium compounds, amine, oxides, and betaines, wherein a surfactant is present at a concentration ranging from about 0.01% to about 2% by weight of said formulation. In one embodiment, the surfactant is polyoxyethylene sorbitan monooleate (polysorbate 80) at a concentration ranging from about 0.02% to about 0.5% by weight of said formulation.

A plasticizer can be selected from the group consisting of glycerol, dimethylsulfoxide (DMSO), propylene glycol, ethylene glycol, oligomeric polyethylene glycol, sorbitol, and combinations thereof, wherein a plasticizer is present at a concentration ranging from about 0.1% to about 5% by weight of said formulation.

Divalent cation can be selected from the group consisting of a pharmaceutically acceptable salt of magnesium, zinc, calcium, manganese, and their combinations thereof, at a concentration ranging from about 1 mM to about 5 mM. In one embodiment, the divalent cation is calcium at a concentration ranging from about 1 mM to about 5 mM.

Amino acid can be alanine, arginine, methionine, serine, lysine, histidine, glycine, glutamic acid, and combinations thereof, wherein an amino acid is present at a concentration ranging from about 0.1% to about 10% (w/v) Amino acids can also be provided by enzymatic digests of proteins. For example, NZ-Amine, an enzymatic digest of casein, can be used to provide a combination of amino acids. In one embodiment, the amino acid is arginine present at a concentration ranging from about 1% to about 8% (w/v).

The aqueous composition can be in a vial, either glass or plastic/resin, a dual cartridge device, a foil pouch device or any other microwave compatible device. A typical load for a microwave drying apparatus is 50-200 vials of 0.5 ml-1 l fill in a 3 cc vial with a maximum capacity of the instrument of 300-350 3 cc or 2R vials. The total vial load is a function of microwave apparatus design.

It is preferable to freeze vaccine via flash freezing or fast freezing approach, especially for high disaccharide containing formulations, to minimize phase separation during freezing and/or potency loss due to extended time in solution for thermolabile vaccines. The purpose of freezing is to (a) transform liquid solution phase to a frozen state (i.e., ice formation), (b) develop an ice structure and distribution in the frozen state to facilitate drying (i.e., porosity), and (c) crystallize the crystalline bulking agents to prevent unwanted crystallization during drying or storage (e.g., annealing). Freezing is usually carried out below the glass transition temperature (Tg' for amorphous matrix) or below eutectic temperature (Teu for crystalline components) for sufficient period of time to allow complete transformation of liquid into a frozen solid state. Liquid solution can be converted to frozen state either using slow freeze (provides larger ice crystals), fast freeze (provides smaller ice crystals) or flash freeze.

Improved thermostability of RSV in presence of enabled high disaccharide formulations can also be obtained by one skilled in the art using alternate processing/drying methods such as spray freeze-drying (SFD) and carbon dioxide-assisted nebulization with a bubble dryer (CAN-BD). Spray-freeze drying involves drying of a frozen spray by sublimation at low pressure with subsequent processing of the dried powder. Similarly, the CAN-BD process consists of combining near critical $CO_2$ with liquid feed for nebulizing the fluid into a fine spray for drying. See, e.g., McAdams et al., Expert Rev Vaccines 2012, 11(10), 1211-1219.

In one embodiment, the method of making dried pellets of a biological material according to the invention comprises loading an aliquot of a liquid composition (such as a liquid protein formulation) comprising the biological material into a dispensing tip and dispensing the aliquot onto a solid, flat surface in such a way that the droplet remains intact while being dispensed. The term "solid, flat surface" means that there are no cavities or wells on the surface where the biological material is being dispensed. Alternatively, the biological material can be dispensed into a cavity or well on a solid surface. Dispensing tips useful in the present invention include those with a round open end, and a pointed open end. Multiple dried pellets may be prepared simultaneously by loading simultaneously the desired number of aliquots of the liquid composition into a multichannel pipettor. Such dried pellets can be in the form of a lyosphere as the "bead" geometry facilitates drying of high solid content formulation in a relatively short time (<24 hrs) compared to traditional vial image drying in a freeze-dryer (~7 days for 1 ml/3 cc vial). See International Patent Application Publication No. WO2013/066769.

Annealing (i.e., short-term re-heating of frozen product) is usually carried to allow efficient crystallization of bulking agent and/or water or to increase the size of ice crystals (Ostwald ripening). Annealing temperature is usually between Tg' and Teu of the bulking agent. In one embodiment, the frozen pellets of vaccine are obtained by aliquoting the formulation (10 µl to 500 µl) on a chilled mold or a surface having a temperature less than or equal to −100° C. Similarly, the frozen cakes are obtained by filling a container, e.g., a vial, with the formulation and subjecting the container to freezing (mostly less than −40° C.) below the glass transition temperature at varying freezing rate (0.1-20° C./min).

The frozen formulations are then subjected to drying using a lyophilizer or a microwave vacuum dryer in a controlled manner to obtain the dried pellets/cake.

In certain embodiments, the frozen formulation is lyophilized according to methods known to those skilled in the art.

Lyophilization (also known as freeze-drying) is the method consisting of freezing the product followed by drying it through sublimation. The lyophilization process consist of three distinct steps: freezing (which can be a slow-freeze, fast freeze or a flash freeze), followed by primary drying wherein most of the unbound water is sublimated and the last step is secondary drying wherein the bound water is removed by desorption. See, generally, Bhambhani et al., 2010, Am. Pharm. Review, 13(1):31-38. Successful lyophilization involves optimization of all three steps. Primary drying is usually carried out at or below the collapse temperature of product while secondary drying is used to optimize the residual moisture content of the dried product.

During lyophilisation, removal of the water and substitution by a matrix comprising protective molecules such as sugar molecules, may increase the stability of the protein by preventing degradation and denaturation of this protein. However, the type and amount of matrix required to stabilize a molecule will vary from product to product and for certain thermolabile viruses such as RSV a high concentration of sugar is required. As a result, when high amounts of sugars are used, and the frozen body has a considerable thickness (typically above 2 mm), this leads to very long drying times in the range of 72-96 hours. When the amount of non-polymeric sugar comes close to 20% w/w, the resulting matrix becomes so dense that drying times increase exponentially. Therefore, a maximum limit of about 15-16% w/w is applied when aiming at homogenously dried bodies. Long drying times inherently lead to a significant loss in biologic activity of the protein and are very unattractive from a manufacturing point of view.

In certain embodiments, after the pellets are frozen, they are subjected to microwave vacuum drying (MVD). MVD provides a unique opportunity to achieve faster sublimation and in some cases alter the stability profile of thermolabile viruses by the virtue of an alternate heat transfer and mass transfer mechanism, compared to the traditional freeze-drying approach. Furthermore, freeze-drying is considered an expensive unit operation due to significant capital investment, utility requirements and lengthy drying times. The lengthy drying times in freeze-drying are attributed to the fact that product temperature cannot be directly controlled during the primary drying as it depends on properties of container, formulation, shelf temperature, and chamber pressure of freeze-dryer system. Thus, a highly skilled scientist is required to perform a number of time-consuming experimental studies to obtain optimal lyophilization cycles and in most cases, sub-optimal" or "conservative" lyophilization cycles are used to dry sensitive products. The low temperature of freeze drying also does not guarantee stability post-drying due to denaturation at interfaces, cold denaturation or other freezing and drying stresses.

The microwave vacuum drying apparatus is capable of providing microwave radiation and a vacuum. Suitable apparatuses are described in U.S. Patent Application Publication Nos. US20120291305, US20100218395, and International Patent Application Publication No. WO2013/010257. A suitable apparatus provides the required uniform drying at the required power application in the required time.

Microwaving refers to the use of non-ionizing electromagnetic radiation to actively induce the evaporation of polar molecules (e.g., water) from a biological composition. Microwaves are electromagnetic waves having operating frequencies anywhere from 0.3 GHz to 300 GHz. While frequencies anywhere within this range can be used, commercially available microwaves typically have frequencies of 2450 MHz and 915 MHz, both of which may be used, but 2450 MHz is preferred. The vibration of polar molecules in a constantly changing electrical field of microwave radiation increases the temperature of the system quickly. Increase of temperature is perhaps the most important factor associated with microwave radiation and the majority of the effects on biological materials are directly related to the heating effect.

A vacuum is pulled to produce a low pressure in the chamber of between 20 to 500 mTorr, 20 to 200 mTorr, 20-100 mTorr or 20-70 mTorr. The higher the vacuum pressure, i.e., the less vacuum, the longer the drying time and the higher the temperature required for drying. Sublimation rate is directly proportional to the differential pressure between the ice-water interface and the chamber pressure. It is therefore preferred to use the highest achievable vacuum pressure differential and minimize the time and temperature required to dry the vaccine.

The level of vacuum also controls the temperature of the vaccine composition being dried. In certain embodiments, the reduced pressure is also utilized to ensure the temperature in the vacuum chamber during drying remains below 35° C.

Drying time is controlled by the amount of vacuum and the power applied to the vaccine composition in the chamber. The higher microwave power applied to the vaccine composition the shorter the required drying time, but if the power is too high for too long deactivation of a live virus can occur. Too low an application of microwave power applied to the vaccine composition is detrimental as it extends drying time. It is preferred to operate using the lowest vacuum pressure (and thus the lowest drying temperature) and the highest application of microwave power in the chamber provided the power is not applied to the extent to damage the vaccine composition being processed to complete the drying quickly while subjecting the vaccine composition to a minimum required drying temperature. In certain embodiments of the invention, the composition is sublimated in less than 12 hours. In other embodiments, the composition is sublimated in the range of 6 to 10 hours, or 3 to 8 hours.

The maximum output power of the microwave may vary in the range of 50 Watt (W) to 900 W per magnetron. Up to 8-16 magnetrons can be used. In one embodiment, the microwave maximum output power per magnetron may be 600 W. In another embodiment, the microwave maximum output power per magnetron may be 400 W (e.g., for a single run consisting of 50-200 vials).

Generally the microwave power applied will be in the range of between 0.5 and 8 KW/hr/Kg of the enveloped virus formulation being dried. The use of low power application is not preferred as the process may become too slow. Application of high power, i.e., above about 8 KW/Kg of the vaccine composition makes controlling the uniformity of the drying process at low moisture content more difficult. Generally an application of microwave power of about 4 KW/Kg of the vaccine composition is preferred.

It is also important to ramp up the microwave power to maintain the integrity of the vaccine composition. This can be achieved by slowly increasing the power at short intervals. Slower ramp (2 W/min) is preferred over stepping the power at bigger time interval (e.g. it is preferred to ramp up the power by 10 W every 10 min then going from 100 W to 250 W after 2.5 hrs). Such a ramping approach, in comparison to stepping up the power significantly, allows for gradual sublimation without compromising the product quality. In certain embodiments, the total energy in the first half of the cycle is only 15%, 20%, 25%, or 30% of the total energy required to dry the system. The ratio of power distribution between the power used in first half cycle and total drying power is usually in 15%-50%, 15-30%, or 15-20% range. Generally, to achieve the ramp up in microwave power, an initial cycle consists of a single magnetron. Additional magnetrons are added to the system as additional cycles are run. In general, any number of cycles can be used to provide the required microwave radiation. In certain embodiments, 3 to 8 cycles are used, for example 5 cycles, the cycle times are generally 30 minutes to 2 hours, and the total microwave energy output is generally in the range of 0.75 kWh to 8.0 kWh and is a function of total number of vials and product intrinsic characteristics.

In certain embodiments, the microwave radiation is applied in a continuous or semi-continuous mode or a batch mode. This selection is contingent on the process and product requirement. Semi-continuous and continuous mode allows for higher throughput while batch process may be used for an established apparatus design or a limited number of vial required.

As discussed above, the reduced pressure ensures that the temperature in the chamber is less than 40-45° C. In one embodiment, the temperature of the product is monitored does not exceed 35° C. The product temperature can be monitored using an IR sensor or a thermal imaging camera.

In certain embodiments, the microwave radiation is applied in a traveling wave format. With a traveling wave applicator, microwaves passes once through sample. This results in better temperature control and uniform product drying. Less preferred is resonance cavity where microwaves pass multiple times through sample. This results in thermal runaway (i.e. overheating) as the sample dries. A single pass microwave allows for controlling the product temperature by limiting the interaction between product and microwave. In contrast, electric field overlap in resonance cavity inhibits controlled interaction and often results in formation of hot and cold spots thus rendering uneven heating and thereby uneven sublimation of the product.

Post-drying, stability of RSV is monitored under accelerated stability conditions (25° C.-37° C. for 1-2 weeks) and the titer loss is determined using RSV plaque assay (pfu/ml). Benchmark titer loss for drying was set at "less than 0.3 log", and the preferred total loss during drying and subsequent 25° C./1 week storage was set at "less than 0.4 log" while the preferred 37° C./1 week incubation loss during storage was set at "less than 1 log".

Additionally, integration of the pelletized (or lyosphere) form of RSV into the primary device after drying allows formation of variety of dosage sizes by choosing the volume of the droplet used to prepare each pellet and the number of pellets added to a single or multiple dosage container or delivery device. For illustration purposes, it can be stated that 100,000 pfu/ml virus titers can be achieved by having 20 beads each of 5,000 pfu/ml bead or 10 beads of 10,000 pfu/ml.

The final dried product may be reconstituted in an appropriate solution for administration of the vaccine to a patient.

The following examples serve only to illustrate the invention and its practice. The examples are not to be construed as limitations on the scope or spirit of the invention.

EXAMPLES

Example 1: Drying High Disaccharide Formulations that Enhance RSV Stability

Live attenuated virus RSV was obtained according to U.S. Patent Application Publication No. 20110212130. Three different test formulations were tested. Formulation 1 consisted of 15% w/v sucrose and 15% w/v trehalose, Formulation 2 consisted of 25% w/v trehalose while Formulation 3 consisted of 25% w/v trehalose and 3% w/v dextran. These formulations were prepared by mixing equal volumes of RSV in harvested media with concentrated solutions of the sugars (2 fold) in water. Formulation 3 was expected to be more difficult with respect to removing residual moisture due to the presence of the high molecular weight dextran (mean molecular weight above 1000 Da). Frozen beads of these compositions were obtained by dispensing 20 μl liquid on a solid, flat metal plate having a surface temperature of approximately −180° C. (see International Patent Application Publication No. WO2013/066769).

The frozen beads were lyophilized on a metal tray using a single step drying at 15° C./30 mTorr for 24 hours to achieve a target residual moisture content of 1-2% w/w. Actual percentages were 1.8% w/w and 1.6% w/w for Formulations 1 and 2 respectively. Formulation 3 was expected to have about 3-5% residual moisture under these drying conditions. No visible differences were observed in pre- and post-lyophilized samples immediately after lyophilization. The lyophilized samples were incubated at 25° C. for 1 week and titer loss was determined using RSV plaque assay. See U.S. Patent Application Publication No. 20110212130. Frozen samples were used as a control in this experiment to determine the drying process loss and loss post incubation at 25° C. for 1 week. Benchmark titer loss for drying was set at "less than 0.3 logs", and preferred total loss during drying and subsequent room temperature storage was set at "less than 0.4 logs".

The dried formulations were tested post-reconstitution with sterile water for injection. All lyophilized samples went immediately into solution after water reconstitution and no particulates were observed in any sample vials while all frozen samples took about 3 minutes to thaw at room temperature. The drying loss and infectivity loss post incubation at 25° C. for 1 week are further described in Table 1 below as $\log_{10}$ losses. All formulations met the drying loss target of "less than 0.3 logs". Formulation 1 and Formulation 2 additionally met the total loss target of "less than 0.4 logs".

TABLE 1

Log$_{10}$ Loss of lyophilized droplets consisting of RSV, as monitored using RSV plaque assay. The data represents an average of 3 measurements.

|  | Formulation 1 | Formulation 2 | Formulation 3 |
|---|---|---|---|
| Drying Loss (Frozen-Dried) | 0.11 | 0.09 | 0.18 |
| Infectivity Loss (25° C./1 wk) | 0.08 | 0.15 | 0.27 |
| Total Loss (Frozen-25° C./1 wk) | 0.19 | 0.24 | 0.45 |

In an independent experiment, lyophilized beads containing RSV and vial compositions of microwave dried RSV were tested under accelerated stability conditions.

TABLE 2

Log10 Loss of lyophilized droplets consisting of RSV, as monitored using RSV plaque assay. The data represents an average of 2 measurements.

| RSV Formulation (20 ul pellets) | Drying loss | Δ Virus titers post incubation at 37° C./1 week | Δ Virus titers post incubation at 37° C./2 week |
|---|---|---|---|
| 25% Sucrose | 0.00 | 0.45 | 0.84 |
| 25% Trehalose | 0.00 | 0.53 | 0.92 |

TABLE 3

Log$_{10}$ Loss of Microwave Vacuum Dried cakes in vial consisting of RSV, as monitored using RSV plaque assay as described in International Patent Application Publication No. WO2013/066769. The data represents an average of 6 measurements.

| RSV Formulation (0.5 ml/3 cc vial) | Drying loss | Δ Virus titers post incubation at 25° C./1 week | Δ Virus titers post incubation at 37° C./1 week |
|---|---|---|---|
| 12.5% Sucrose. 10 mM Histidine 10 mM Tris pH 7.0 | 0.13 | 0.57 | 1.05 |
| 25% Trehalose 50 mM Histidine 50 mM Arginine 10 mM Bis-Tris pH 7.0 | 0.07 | 0.30 | 0.71 |

In this example, thermostable (high disaccharide) RSV compositions were obtained by utilizing frozen lyospheres that were freeze-dried as well as a vial image that was microwave vacuum dried. It is important to note that these high disaccharide formulations would be very difficult to dry using the standard approach of freezing-drying vials of vaccine to produce dried cakes. Furthermore, it was shown that formulation optimization was necessary to obtain enhanced thermostability for RSV and not all high disaccharide compositions were able to improve the stability of RSV. For example, both Formulation 2 and Formulation 3 (Table 1) contain 25% Trehalose but greater stability was observed for Formulation 2 compared to Formulation 3.

These studies demonstrate similar stabilization and drying results by using either sucrose or trehalose at high concentration (25% in these cases) and that the presence of low sucrose was not beneficial to attain the stability of the live attenuated RSV.

Example 2: RSV Stability in Previously Described Liquid Formulations

Various formulations corresponding to those described in the prior art were tested for stability. Prior findings suggested that RSV stability was maintained best at sucrose concentrations >30% at sub-zero temperatures with greatest stability observed at −70° C. See Law et al., Experimental biology and Medicine 1968; 128: 515-518. Similarly, others findings revealed that sub-zero stabilization of RSV at sub-zero conditions in the presence of sugars (25% sucrose or 10% trehalose or 10% sorbitol) effectively maintains stability. See Gupta et al., Vaccine 1996; 14:1417-20. However, accelerated stability studies at 37° C. of the above mentioned formulation resulted in a significant potency loss as described below in Table 4 (observed losses were >1 log post 37° C./1 week incubation).

TABLE 4

Stabilizing effect of various liquid formulations used for stabilizing RSV

| RSV Formulation | Days at 37° C. | Δ Virus titters ($\log_{10}$ TCID$_{50}$ ml$^{-1}$) | Extrapolated loss post 37° C./1 week incubation | Ref |
|---|---|---|---|---|
| 25% Sucrose in phosphate buffered saline pH 7.2 | 3 | 0.67 | 1.56 | i |
| 25% Sucrose in Water | 3 | 0.52 | 1.21 | i |
| 10% Trehalose 10% foetal bovine serum in eagles' minimum essential medium pH 7.8 | 3 | 1.35 | 3.15 | i |

TABLE 4-continued

Stabilizing effect of various liquid formulations used for stabilizing RSV

| RSV Formulation | Days at 37° C. | Δ Virus titters ($\log_{10}$ $TCID_{50}$ $ml^{-1}$) | Extrapolated loss post 37° C./ 1 week incubation |

9. The method according to claim 8, wherein the pressure is a pressure in the range of 20 to 200 mTorr.

* * * * *